United States Patent [19]
Marion et al.

[11] Patent Number: 6,100,438
[45] Date of Patent: *Aug. 8, 2000

[54] PROCESS FOR PRODUCING A TERTIARY OLEFIN BY DECOMPOSING A TERTIARY ALKYL ETHER

[75] Inventors: Marie-Claire Marion, Villeurbanne; Vincent Coupard, Lyons; Alain Forestière, Vernaison; Philippe Travers, Rueil Malmaison; Jean-Charles Viltard, Valence, all of France

[73] Assignee: Institut Francais du Petrole, Rueil-Malmaison Cedex, France

[ * ] Notice: This patent is subject to a terminal disclaimer.

[21] Appl. No.: 09/026,682

[22] Filed: Feb. 20, 1998

[30] Foreign Application Priority Data

Feb. 21, 1997 [FR] France .................................. 97 02194

[51] Int. Cl.⁷ ..................................................... C07C 1/00
[52] U.S. Cl. .......................... 585/639; 585/640; 585/642
[58] Field of Search .................................... 585/639, 640, 585/642

[56] References Cited

U.S. PATENT DOCUMENTS

4,447,668 5/1984 Smith, Jr. et al. ....................... 585/639
5,354,831 10/1994 Panster et al. .............................. 528/9

FOREIGN PATENT DOCUMENTS

2669021 5/1992 France .

*Primary Examiner*—Bekir L. Yildirim
*Attorney, Agent, or Firm*—Millen, White, Zelano & Branigan, P.C.

[57] ABSTRACT

A process for producing a tertiary olefin by decomposing a tertiary alkyl ether comprises a) decomposing at least one ether to a product containing an alcohol and a tertiary olefin, b) fractionating at least a portion of the product from a) in a fractionation zone (C1) to obtain the tertiary olefin and the alcohol, c) purifying at least a portion of the tertiary olefin obtained from step b) wherein said portion is sent to a water washing extraction zone (L1) from which a fraction (D) containing the tertiary olefin is recovered, and d) a step in which at least a portion of the fraction (D) from c) is sent to a separation zone (Co) from which a liquid aqueous fraction (Le) and a liquid hydrocarbon fraction (Lc) containing the major portion of the tertiary olefin are recovered.

21 Claims, 1 Drawing Sheet

Figure
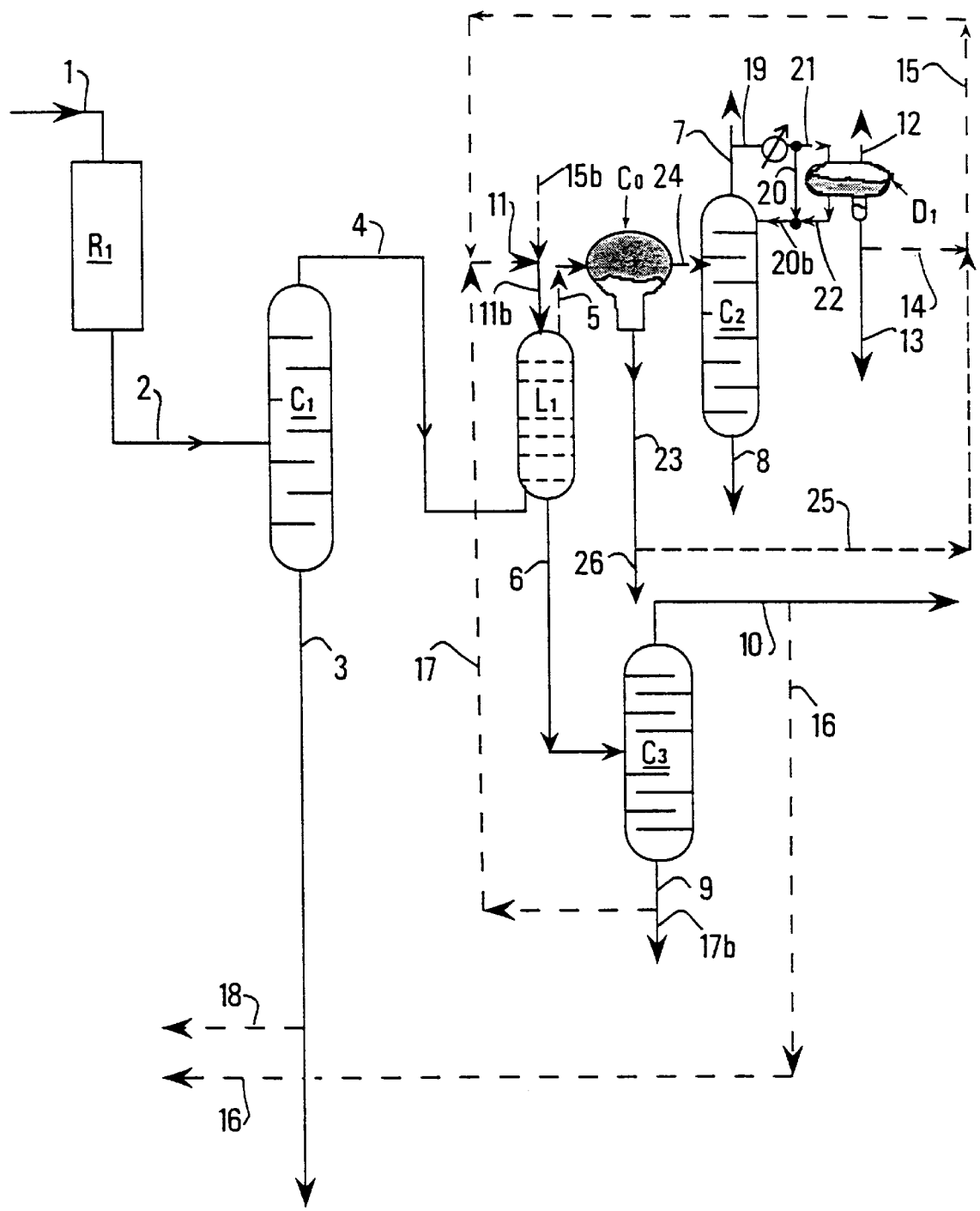

PROCESS FOR PRODUCING A TERTIARY OLEFIN BY DECOMPOSING A TERTIARY ALKYL ETHER

FIELD OF THE INVENTION

The invention relates to a process for decomposing tertiary alkyl ether(s) to produce high purity tertiary olefin(s). In particular, it relates to a process for the production of very high purity isobutene and methanol from methyl-tertio-butyl-ether (MTBE). The process of the present invention is also applicable to the synthesis of any tertiary olefin from a tertiary alkyl ether [for example ETBE (ethyl-tertio-butyl-ether), ETAE (tertio-amyl-methyl-ether), TAME (terti-amyl-methyl-ether, and isopropyl-tertio-butyl-ether]. The remainder of the description, in particular the operating conditions, is given by way of indication for the synthesis of isobutene from MTBE.

BACKGROUND OF THE INVENTION

A variety of routes for producing high purity isobutene can be employed industrially. The oldest is the sulphuric acid extraction process, but it is expensive and obsolete; it is known to be a contaminating process as waste acid is discharged. Further, the isobutene yield does not exceed 90%. The company ARCO uses tertio-butyl alcohol (TBA) dehydration, TBA being a by-product obtained from their propylene oxide production process. The isobutane dehydrogenation process was developed during the last few years as a result of the large and increasing demand for MTBE. However, that process can only be profitable with very large production capacities.

High purity isobutene production from cracking MTBE is as suitable for small capacities as for large capacities. Further, such a route benefits from the infrastructure generated by the increasing importance of ethers in reformulated gasoline. A number of refineries throughout the world have MTBE production installations, for example. Further, there is a global exchange market for MTBE. This means that the production of high purity isobutene from MTBE can readily be carried out anywhere in the world, in and remote from refineries.

The concept of producing isobutene by decomposing an ether, more particularly MTBE, has long been known, but prior art processes have suffered from certain disadvantages.

In the process developed by SUMITOMO described, for example, in European patent application EP-A-0 068 785, the MTBE decomposition reaction is carried out in the liquid phase, in the presence of a solid acid catalyst which is an ion exchange resin. Two product streams are obtained: isobutene and methanol. As described, isobutene is obtained directly overhead from a distillation column with no other purification step. The isobutene obtained contains a certain number of impurities, beginning with a small fraction of methanol which is azeotropically distilled from dimethylether (DME), which is a volatile compound formed by condensing methanol in the presence of an acid catalyst. It is probable that the purity of the isobutene is insufficient for use in, for example, the production of polyisobutene or other copolymers. Further, there is no apparent way of avoiding the accumulation of heavy impurities such as dimers of isobutene or methyl sec-butyl ether (MSBE), which in the long run results in a fatal reduction of product purity.

In the process developed by ERDOLCHEMIE, described in U.S. Pat. No. 4,409,421, for example, isobutene is purified by eliminating residual alcohol entrained with the tertiary olefin by adsorption. This method has the disadvantage of requiring regular regeneration of the adsorbent. Further, the problem of recovery of the major portion of the alcohol from the decomposition step is not solved.

SUMMARY OF THE INVENTION

More recently in U.S. Pat. No. 5,095,164, the same company has described carrying out the decomposition reaction in a distillation apparatus. The catalyst is placed in the bottom of the column at the reboiler level. That particular implementation limits the reaction temperature, which is directly imposed by the nature of the ether and the operating pressure. Further, it apparently encourages the formation of reaction by-products such as the formation of dimers of isobutene and/or dimethylether formation. In this regard, the quality and/or development or the products is not clearly explained.

In U.S. Pat. No. 4,287,319, BASF describes a scheme which integrates both ether synthesis, its separation then the ether decomposition step to produce the isobutene. However, in order to avoid certain purification steps, etherification is carried out with a $C_3$ or $C_4$ alcohol, which is a major disadvantage as regards the international MTBE market.

Finally, we can cite the two schemes of the SNAMPROGETTI process presented in "Chemical Economy & Engineering Review", vol. 14, n° Jun. 6, 1982, including both the MTBE synthesis step and the MTBE decomposition step for the production of isobutene. In such schemes, it appears that a certain loss of water by entrainment and/or saturation of the isobutene stream when washing to eliminate the alcohol has not been taken into account. This can eventually lead either to a reduction in the washing water flow rate, or to a loss of efficiency in that washing section. That can deleteriously affect the quality of the isobutene produced. Further, in such schemes all of the hydrocarbon fraction from the water extraction column which contains a relatively large amount of free water is sent to the fractionation column to recover purified isobutene which implies that that column has to treat a large quantity of product and must therefore have large dimensions which renders the process particularly expensive and difficult to carry out.

The process of the invention can overcome the above disadvantages. It concerns a process for the production of tertiary olefin(s) from a tertiary alkyl ether, characterized by a very high purity.

The invention concerns a process for decomposing tertiary alkyl ether(s), in particular those defined above, preferably MTBE or ETBE, to produce high purity tertiary olefin(s), in particular isobutene. When decomposing other ethers, a mixture can be obtained which contains a plurality of tertiary olefins. Thus in the case of TAME decomposition, a mixture containing 2-methyl-1-butene and 2-methyl-2-butene is obtained.

In addition to the reaction zone itself, the process of the invention comprises zones for purification, recovery or recycling the various products to optimise upgrading of the products used and to minimise losses.

The present invention provides a process for producing a tertiary olefin by decomposing a tertiary alkyl ether, comprising:

a) a step for decomposing at least one tertiary alkyl ether in a reaction zone comprising at least one reactor (R1) containing a catalyst for decomposing said ether, the step being carried out under conditions which can at least partially decompose said tertiary alkyl ether to a product containing at least one alcohol and at least one tertiary olefin;

b) a step for fractionating at least a portion, preferably all, of the product from step a) in a fractionation zone (C1) to obtain a fraction (A) containing the major portion of the tertiary olefin and possibly a minor fraction of alcohol and any light compounds generally initially contained in the product from step a), and a fraction (B) containing the major portion of the alcohol formed in step a) and possibly ether which has not been decomposed in step a);

c) a step for purifying at least a portion of fraction (A) in which said portion is sent to a water washing extraction zone (L1) from which an aqueous fraction (C) is obtained containing the major portion of the alcohol initially present in said portion, and a fraction (D) containing the major portion of the tertiary olefin initially present in said portion, said fraction (D) containing said tertiary olefin, water and possibly light compounds and being substantially free of alcohol;

said process being characterized in that it comprises a step d) in which at least a portion of fraction (D) from step c) is sent to a separation zone (Co) from which an aqueous liquid fraction (Le) and a liquid fraction (Lc) containing the major portion of the tertiary olefin initially present in fraction (D) are obtained, said fraction (Lc) containing said tertiary olefin, a small quantity of water and possibly light compounds.

In a particular implementation of the process of the invention, which generally produces a high purity tertiary olefin, at least a portion of the liquid fraction (Lc) recovered from step d) is sent to a step e) in a fractionation zone (C2) in which said portion of fraction (Lc) is fractionated into a fraction (E) containing the tertiary olefin and a fraction (F) containing the major portion of any light compounds and possibly a small quantity of residual water. Fraction (F) can be split into a gaseous fraction which can be flared off, for example, and a liquid fraction at least part of which is returned to fractionation zone (C2) of step e) [line (20b) from line (20) and/or line (22)].

In this particular implementation, it is generally preferable that the fractionation zone of step e) comprises at least one means for recovering a substantially anhydrous light fraction from fraction (F). This means generally splits at least a portion of fraction (F) into a substantially anhydrous light fraction and an aqueous fraction. The means is, for example, a separator drum provided with at least one means, for example a boot, for decanting and extracting an aqueous fraction. In this case, at least a portion of the aqueous fraction obtained from step e) is preferably recycled to step c) in water washing extraction zone (L1). Thus the substantially anhydrous light fraction is normally split into a gaseous fraction which is flared off, for example, and a liquid fraction which is generally substantially anhydrous which is recycled at least in part to the fractionation zone (C2) of step e). In a further implementation, at least part of fraction (F) [or the light fraction obtained from fraction (F)] which originates from step e) is sent to a catalytic cracking zone. In a further variation, at least part of fraction (F) [or the light fraction obtained from fraction (F)] from step e) is sent to a zone for synthesising ether by reaction between at least one tertiary olefin and at least one alcohol. In yet another variation, at least part of the fraction (F) [or the light fraction obtained from fraction (F)] from step e) is flared off.

The process of the present invention usually comprises a step f) in which at least a portion of the aqueous fraction (C) from step c) is sent to a fractionation zone (C3) from which a fraction (G) containing the major portion of the alcohol initially present in said portion and an aqueous fraction (H) which is free of the major portion of the alcohol initially present in said portion are recovered. In this implementation, at least a portion of fraction (G) obtained from step f) containing alcohol can be sent to a zone for synthesising ether by reaction between at least one tertiary olefin and at least one alcohol. It is also possible to send all of this alcohol to the ether synthesis zone. It is also possible to recover all or part of this alcohol for other uses. In this implementation at least a portion of the aqueous fraction (H) obtained in step f) can also be at least partially recycled to step c) in water washing extraction zone (L1). In this implementation, at least a portion of the aqueous fraction (H) obtained in step f) can also be recycled to step c) to the water washing extraction zone (L1). In this implementation, at least a portion of the aqueous fraction (H) obtained in step f) can also be sent at least in part to a water treatment section.

In a preferred implementation of the process of the present invention, at least a portion of fraction (B) obtained from step b), containing the major portion of the alcohol formed in step a) and possibly ether which has not been decomposed in step a), is sent to a zone for synthesising ether by reaction between at least one tertiary olefin and at least one alcohol. It is also possible to send all of this fraction to the ether synthesis zone. It is also possible to recover all or part of this fraction for other uses.

In a preferred implementation of the process of the present invention, at least a portion of the aqueous fraction (Le) obtained in step d) is recycled to step c) to water washing extraction zone (L1).

These different water recycles are independent of each other and can be carried out together or separately. Water which is not recycled is generally purged then normally sent to a waste water treatment zone. This purge is normally present at least in the aqueous fraction (H) obtained in step f). This purge can in particular avoid any accumulation of heavy compounds, for example heavy alcohols.

The conditions under which step a) of the present invention are carried out are conventional tertiary alkyl ether decomposition conditions which are well known to the skilled person. In a preferred implementation, this step a) is carried out without adding supplementary water to the product introduced into the decomposition zone. However, it is possible to add a certain quantity of water, for example up to the limit of the solubility of water in the ether which is to be decomposed. Normally, the conditions under which step a) is carried out are selected so that the major portion of the tertiary alkyl ether decomposes to produce an alcohol and a tertiary olefin. In this decomposition zone, the absolute pressure is normally about 1 to about 12 bars (1 bar=0.1 MPa), the temperature is normally in the range 50° C. to 300° C., preferably in the range 100° C. to 250° C., the HSV (hourly space velocity) is normally in the range 0.1 to 200 $h_{-1}$, normally in the range 0.5 to 100 $h_{-1}$. In this zone, any of the acid catalysts known to the skilled person can be used. Solid acid catalysts are preferably used. Thus the catalyst can be selected from the group formed by acid organic resins and mineral acid resins, generally solids under the ether decomposition reaction conditions. Of these compounds, those selected from the group formed by grafted mineral solids containing at least one alkylsulphonic arylsulphonic or alkylarylsulphonic type organic group are usually used. In one preferred implementation of this step a), a catalyst selected from the group formed by polysiloxanes grafted with at least one alkylsulphonic group is used.

Step b) for fractionating the product from ether decomposition step a) is a step in which the general conditions are particularly selected as a function of the characteristics of the alcohol and tertiary olefin formed. The skilled person can select these conditions to obtain the desired separation between a fraction containing the major portion of the alcohol and a fraction containing the major portion of the olefin. Thus in the case of MTBE decomposition and the formation of methanol and isobutene, for example, the absolute pressure in the distillation column is about 1 to about 15 bars, preferably about 1 to about 10 bars, identical to or different from that prevailing in the decomposition zone. The bottom temperature of the column depends both on the pressure in the column and the composition of the bottoms product, in particular the molar ratio between the methanol and MTBE which may be present due to partial decomposition of this ether in step a). In the case of a unit treating 1 kg/h of MTBE, the distillation column normally contains 3 to 80 theoretical plates, normally 10 to 50 theoretical plates.

In step c) for purifying at least a portion of fraction (A), the portion of the fraction is sent to a water washing extraction zone (L1); the quantity of water used for this washing is normally such that the ratio between the volume of that quantity of water introduced into the extraction zone and that of the portion of fraction (A) introduced into the extraction zone ($V_{water}/V_A$) is about 0.005 to about 20 by volume. This quantity of water is usually such that the ratio $V_{water}/V_A$ is about 0.005 to about 10, preferably about 0.01 to about 5, more preferably about 0.02 to about 1. The water flow rate in this washing zone (L1) is normally regulated so as to maintain a foundation level in the water and alcohol fractionation zone (C3) when such a zone (C3) is present. This foundation level can be defined as the minimum level required for zone (C3) to operate properly. This parameter is a conventional parameter which is well known to the skilled person. The regulation is often carried out manually by the operators, but it is possible for this regulation to be carried out by an automatic Level Control Regulation circuit. Regardless of the selected mode of regulation, the quantity of water can generally be adjusted using a means for introducing makeup water into zone (L1). This makeup water can compensate for loss of water due to entrainment of water and/or saturation of the treated hydrocarbon stream and replacement of any purged water. This extraction zone (L1) is normally a tray column which operates at a temperature of about 1° C. to about 100° C., preferably about 10° C. to about 60° C. The absolute pressure in this zone is about 1 to about 20 bars, normally about 1 to about 15 bars, identical to or different from that prevailing in the fractionation zone of step b).

Step d), which comprises a zone for separating at least a portion of fraction (D) into an aqueous liquid fraction (Le) and a liquid hydrocarbon fraction (Lc) in a zone (Co), is a conventional step which is known to the skilled person. This step is normally carried out in a coalescer, in which water collects in the lower part of the apparatus by coalescence. The temperature and pressure conditions in this zone are in the same ranges as those in water extraction step c). The pressure (or respectively the temperature) can be identical to or different from that in zone (L1) of step c). In this zone, the free water contained in the product from step c) is separated out. Further, this zone also normally acts as a feed drum for the isobutene purification zone (C2). Any other means known to the skilled person can be used in the present invention. As an example, an absorbent with preferential selectivity for the aqueous or organic fraction could be used.

Optional step e) for fractionating fraction (Lc) in a zone (C2) into a fraction (E) containing the tertiary olefin and a fraction (F) containing the major portion of the light compounds possibly present in fraction (Lc) and residual water contained in liquid fraction (Lc) is normally carried out in a distillation column operating at an absolute pressure of about 1 to about 15 bars, normally about 3 to about 10 bars, identical to or different from that in the separation zone of step d). For a unit producing 0.6 kg/h of isobutene, this column normally has about 3 to about 80 theoretical plates, usually about 5 to about 50 theoretical plates. The bottom temperature of the column depends in particular on the pressure in the column.

The optional fractionation step f) in a zone (C3) of the aqueous fraction (C) containing the major portion of the alcohol initially present in fraction (A) into a fraction (G) containing the major portion of the alcohol initially present in fraction (C) and an aqueous fraction (H) which is free of the major portion of the alcohol initially present in fraction (C) is normally carried out in a distillation column (C3) at an absolute pressure of about 1 to about 12 bars, preferably about 1 to about 8 bars, identical to or different from that in the water extraction zone of step c). The bottom temperature in the column particularly depends on the pressure in the column; it is normally about 50° C. to about 300° C., usually about 65° C. to about 200° C. The column normally has about 2 to about 80 theoretical plates, usually about 3 to about 60 theoretical plates.

FIG. 1 is a flowsheet illustrating one preferred variation of an implementation of the present invention. The dotted lines show the various possible options.

The feed containing the tertiary alkyl ether is introduced into an ether decomposition reactor (R1) via a line 1. The reactor contains an acid catalyst. The decomposition product leaves reactor (R1) and is sent via a line 2 to a fractionation column (C1), from which a product containing a tertiary olefin is recovered via a line 4 and a product containing an alcohol and possibly ether which has not been decomposed is recovered via a line 3. Part of the product leaving column (C1) via line 3 can, for example, be sent via a line 18 to a tertiary alkyl ether synthesis zone. The product containing the tertiary olefin is introduced via line 4 into a water extraction zone (L1), where water is introduced via line 11b and from which a fraction (D) which is depleted in alcohol is recovered via line 5 and sent to a separation zone (Co) from which an aqueous liquid fraction (Le) is recovered via line 23 and a liquid hydrocarbon fraction (Lc) containing the major portion of the tertiary olefin initially present in fraction (D) is recovered via line 24, the fraction (Lc) containing the tertiary olefin, a small quantity of water and possibly light compounds being sent via line 24 to a fractionation zone (C2). An aqueous product containing alcohol is recovered via a line 6 and introduced into a fractionation zone (C3). The tertiary olefin, which is usually ultra pure, is recovered via a line 8 from fractionation zone (C2) and light products are recovered via a line 7, part of which are flared off, for example, but which can also be sent to a catalytic cracking zone or to an ether synthesis zone, and recycled in part to fractionation zone (C2) as a reflux via lines 19, 20 and 20b. In a preferred embodiment, it is also possible to send at least part of these light products via lines 19 and 21 to a separation zone (D1) from which a fraction constituted mainly by water is recovered via a line 13, a liquid fraction of light products is recovered via line 22 and returned to column (C2) as a reflux via line 20b; at least a portion of the light gaseous products are recovered via line 12 and part is flared off, for example, although it can also be sent to a catalytic cracking zone or to an ether synthesis zone. It is also possible to combine the two embodiments described above. The aqueous fraction can be recovered via line 13 or part of it can be returned to water extraction zone L1 via lines 11b, in addition to an optional water makeup via line 15b. Alcohol is recovered from fractionation zone (C3) via line 10 and part of it can, for example, be sent via line 16 to a tertiary alkyl ether synthesis zone. From this zone (C3), an aqueous fraction is also recovered via line 9, at least part of which can be sent to a water treatment zone via line 17b, or it can be recycled at least in part to water extraction zone (L1) via lines 17, 11 and 11b. At least part of the aqueous liquid fraction (Le) recovered from the separation zone (Co) via line 23 can be sent via line 26 to a water treatment zone, or at least part of it can be recycled to water extraction zone (L1) via lines 255, 15, 11 and 1b.

The following examples illustrate the invention without limiting its scope.

EXAMPLE 1

A pilot type unit was used which comprised a 10 ml volume tube reactor (R1), operating at a relative pressure of 7 bars, at an average temperature of 160° C., containing 3 grams of a catalyst which was a polysiloxane grafted with alkylsulphonic groups. A commercial catalyst based on polysiloxanes grafted with at least one alkylsulphonic group was used. Reactor (R1) was supplied with a feed containing 100% by weight of MTBE at a HSV of 15 h$^{-1}$. Table 1 shows the composition of the feed introduced into MTBE decomposition reactor (R1) and the composition of the product recovered from the outlet from reactor (R1).

TABLE 1

|  | Feed (wt %) | R1 effluent (wt %) |
|---|---|---|
| MTBE | 100 | 10 |
| Isobutene |  | 56.1 |
| Methanol |  | 32.1 |
| DME |  | 0.5 |
| Dimers |  | 1.1 |
| H$_2$O |  | 0.2 |

The various purification sections were calculated using software produced by American company SIMSCI (SIMulation SCIence INC.) under the trade name Pro II.

A distillation column (C1) operating at a relative pressure of 7 bars and comprising 10 theoretical plates was used in step b) of the process of the invention to obtain a bottoms product (B) and an overhead product (A).

A water extraction column (L1), a tray column operating at a temperature of 30° C. at a relative pressure of 12 bars, was used in step c) of the process of the invention to obtain an aqueous fraction (C) and an organic fraction (D).

A coalescer type (Co) system for extracting free water entrained in step c) in fraction (D) produced an aqueous fraction (Le) and an organic fraction (Lc). It operated at a relative pressure of 12 bars and at a temperature of 30° C.

A distillation column (C2), the last step in the isobutene purification, operating at a relative pressure of 7 bars and comprising 10 theoretical plates, was used in step e) to obtain a bottoms product (E) which was purified isobutene and an overhead product (F) containing light compounds.

Column (C1) was supplied by the effluent from (R1). Product (A) recovered overhead from (C1) was sent to extraction column (L1) where it was washed with a quantity of water the volume flow rate of which was a tenth of the flow rate of (A). An aqueous fraction (C) mainly containing the methanol contained in (A), and a hydrocarbon fraction (D) containing a small quantity of free entrained water, were recovered. This fraction of free water was finally eliminated after decanting in the decanting system (Co) in the form of a fraction (Le), and an organic hydrocarbon fraction (Lc) was recovered. Finally, the hydrocarbon fraction (Lc) was treated in column (C2) to produce a fraction (E) from the bottom of the column, which was high purity isobutene, and a light fraction (F) overhead, containing dimethyl ether (DME).

The material balances are shown in Tables 2 and 3 below.

TABLE 2

|  | Effluent from reactor (R1) (wt %) | Product (B) column (C1) (g/h) | Product (A) column (C1) (g/h) | Washing water column (L1) | Fraction (C) column (L1) | Fraction (D) column (L1) |
|---|---|---|---|---|---|---|
| MTBE | 10 | 10 |  |  |  |  |
| Isobutene | 56.1 |  | 56.1 |  |  | 56.1 |
| Methanol | 32.1 | 30.4 | 1.7 |  | 1.7 | — |
| DME | 0.5 |  | 0.5 |  |  | 0.5 |
| Dimers | 1.1 | 1.1 |  |  |  | — |
| H$_2$O | 0.2 |  | 0.2 | 10 | 9.2 | 1 |
| Flow rate (g/h) | 100 | 41.5 | 58.5 | 10 | 10.9 | 57.6 |

TABLE 3

|  | Aqueous fraction (Le) extracted by (Co) | Organic fraction (Lc) outlet from (Co) | Fraction (F) column (C2) | Fraction (E) column (C2) |
|---|---|---|---|---|
| Isobutene |  | 56.1 | 1.72 | 54.38 |
| DME |  | 0.5 | 0.49 | 0.01 |
| H$_2$O | 0.99 | 0.01 | 0.01 |  |
| Flow rate (g/h) | 0.99 | 56.61 | 2.22 | 54.39 |
| Isobutene purity (%) |  |  |  | 99.9% |
| Isobutene yield (%) |  |  |  | 96% |

Thus the process of the invention can produce very high purity isobutene.

EXAMPLE 2

This was a pilot type apparatus comprising a tube reactor R1 operating at a relative pressure of 7 bars, and at an average temperature of 140° C. Reactor R1 contained Deloxan ASP (a catalyst which is a polysiloxane grafted with alkylsulphonic groups). R1 was supplied with a feed containing 100% by weight of TAME at a HSV of 6 h$^{-1}$. The product recovered from the R1 outlet had the composition given in Table 4:

TABLE 4

| MTBE DECOMPOSITION REACTION SECTION | | |
|---|---|---|
|  | Feed (wt %) | R1 effluent (wt %) |
| TAME | 100 | 15 |
| Isoamylenes |  | 58.2 |
| Methanol |  | 26.45 |
| DME |  | 0.25 |
| Dimers |  | 0.1 |

As in the preceding example, the purification cross sections were calculated using Pro II software.

A material balance summary is given by way of illustration in Table 5.

TABLE 5

| | R1 effluent (wt %) | C1 overhead (g/h) | C1 bottoms (g/h) | Organic fraction D after washing (g/h) | Fraction Lc Co outlet (g/h) |
|---|---|---|---|---|---|
| TAME | 15 | | 15 | | |
| Isoamylenes | 58.2 | 58.2 | | 58.2 | 58.2 |
| Methanol | 26.45 | 2 | 24.45 | | |
| DME | 0.25 | 0.25 | | 0.25 | 0.25 |
| Dimers | 0.1 | | 0.1 | | |
| $H_2O$ | | | | 1.55 | 0.01 |
| Flow rate (g/h) | 100 | 60.45 | 39.55 | 60 | 58.46 |

Isoamylenes were thus produced with a minimum yield of 84% (the yield could be improved by recycling unconverted ether) and with a purity of over 99%.

We claim:

1. A process for the production of a tertiary olefin by decomposing a tertiary alkyl ether, comprising:
   a) a step for decomposing at least one tertiary alkyl ether in a reaction zone comprising at least one reactor (R1) containing a catalyst for decomposing said ether, said step being carried out under conditions which can at least partially decompose said tertiary alkyl ether to a product containing at least one alcohol and at least one tertiary olefin;
   b) a step for fractionating at least a portion of the product from step a) in a fractionation zone (C1) to obtain a fraction (A) containing the major portion of the tertiary olefin and optionally a minor fraction of alcohol and any light compounds, and a fraction (B) containing the major portion of the alcohol formed in step a) and optionally ether which has not been decomposed in step a);
   c) a step for purifying at least a portion of fraction (A) in which said portion is sent to a water washing extraction zone (L1) from which an aqueous fraction (C) is obtained containing the major portion of the alcohol initially present in said portion and a fraction (D) containing the major portion of the tertiary olefin initially present in said portion, said fraction (D) containing said tertiary olefin, water and optionally light compounds and being substantially free of alcohol;
   said process being characterized in that it comprises a step d) in which at least a portion of fraction (D) from step c) is sent to a separation zone (Co) from which an aqueous liquid fraction (Le) and a liquid fraction (Lc) containing the major portion of the tertiary olefin initially present in fraction (D) are obtained, said fraction (Lc) containing said tertiary olefin, a small quantity of water and optionally light compounds.

2. A process according to claim 1, in which at least a portion of fraction (Lc) recovered from step d) is sent to a step e) in a fractionation zone (C2) in which said portion of fraction (Lc) is fractionated into a fraction (E) containing the tertiary olefin and an overhead fraction (F) containing the major portion of any light compounds and a small quantity of residual water.

3. A process according to claim 2, further comprising partially condensing fraction (F) so as to recover a condensate and a substantially anhydrous light fraction from fraction (F).

4. A process according to claim 3, in which the condensate is passed to a separator so as to separate an aqueous fraction.

5. A process according to claim 4, in which at least part of said aqueous fraction is directly recycled to step c) in the water washing extraction zone (L1).

6. A process according to claim 2, in which at least a portion of fraction (F) or a substantially anhydrous light fraction obtained from said fraction (F) is sent at least in part to a catalytic cracking zone.

7. A process according to claim 2, in which at least a portion of fraction (F) or a substantially anhydrous fraction obtained from said fraction (F) is sent at least in part to a zone for synthesising an ether by reaction between at least one tertiary olefin and at least one alcohol.

8. A process according to claim 1, further comprising a step f) in which at least a portion of fraction (C) from step c) is sent to a fractionation zone (C3) from which a fraction (G) containing the major portion of the alcohol initially present in said portion and also an aqueous fraction (H) which is free of the major portion of the alcohol initially present in said portion are recovered.

9. A process according to claim 8, in which at least a portion of fraction (G) is sent to a zone for synthesising an ether by reaction between at least one tertiary olefin and at least one alcohol.

10. A process according to claim 8, in which at least a portion of the aqueous fraction (H) is sent at least in part to a water treatment section.

11. A process according to claim 8, in which at least a portion of the aqueous fraction (H) is directly recycled at least in part to step c) in the water washing extraction zone (L1).

12. A process according to claim 1, in which at least a portion of fraction (B) is sent to a zone for synthesising an ether by reaction between at least one tertiary olefin and at least one alcohol.

13. A process according to claim 1, in which at least a portion of the aqueous fraction (Le) obtained in step d) is directly recycled at least in part to step c) in the water washing extraction zone.

14. A process according to claim 1, in which, in step c) for purifying at least a portion of the fraction (A), a quantity of water is introduced into the water washing extraction zone (L1) such that the ratio between the volume of said quantity of water introduced into said extraction zone and that of said portion of fraction (A) ($V_{water}/V_A$) is 0.005 to 20 by volume.

15. A process according to claim 1, in which the water washing extraction zone (L1) in step c) comprises at least one means for introducing makeup water.

16. A process according to claim 1, in which the catalyst of step a) is selected from the group formed by organic acid resins and mineral acid resins.

17. A process according to claim 1, in which the catalyst of step a) is a mineral solid having a grafted group selected from the group consisting of at least one organic alkylsulphonic, arylsulphonic and alkylarylsulphonic radical.

18. A process according to claim 1, in which he catalyst in step a) is a polysiloxane grafted with at least one alkyl-sulphonic group.

19. A process according to claim 4, further comprising a step f) in which at least a portion of fraction (C) from step c) is sent to a fractionation zone (C3) from which a fraction (G) containing the major portion of the alcohol initially present in said portion and also an aqueous fraction (H) which is free of the major portion of the alcohol initially present in said portion are recovered.

20. A process according to claim 19, in which at least a portion of the aqueous fraction (H) is directly recycled at least in part to step c) in the water washing extraction zone (L1).

21. A process according to claim 20, in which at least a portion of the aqueous fraction (Le) obtained in step d) is directly recycled at least in part to step c) in the water washing extraction zone.

* * * * *